United States Patent [19]

Bradley

[11] Patent Number: 5,868,928
[45] Date of Patent: Feb. 9, 1999

[54] MICROBIAL SAMPLER AND CONCENTRATOR

[76] Inventor: Bruce J. Bradley, 801 N. Lincoln, Jerome, Id. 83338

[21] Appl. No.: 872,268

[22] Filed: Jun. 10, 1997

[51] Int. Cl.⁶ ................................................. B01D 63/00
[52] U.S. Cl. ................. 210/257.2; 211/202; 211/206; 211/260; 211/262; 211/321.6; 211/321.69; 211/360.1; 211/391; 211/406; 211/411; 211/412.1; 134/104.4; 134/109
[58] Field of Search ................ 210/198.1, 202, 210/206, 251.1, 257.2, 254, 262, 260, 321.6, 321.69, 323.1, 333.01, 360.1, 391, 406, 411, 416.1; 134/10, 21, 33, 104.4, 109; 435/30, 39

[56] References Cited

U.S. PATENT DOCUMENTS

| | | | |
|---|---|---|---|
| 3,963,615 | 6/1976 | Plakas | 210/202 |
| 4,792,398 | 12/1988 | Klein | 210/406 |
| 4,919,825 | 4/1990 | Croket | 210/783 |
| 5,108,381 | 4/1992 | Kolozsi | 604/319 |
| 5,223,133 | 6/1993 | Clark et al. | 210/232 |
| 5,227,075 | 7/1993 | Ostman | 210/781 |
| 5,482,626 | 1/1996 | Lohnes et al. | 210/340 |
| 5,490,531 | 2/1996 | Bala et al. | 134/109 |
| 5,704,989 | 1/1998 | Page | 134/10 |

OTHER PUBLICATIONS

Vacuum Probe: New Approach to the Microbiological Sampling of Surfaces, Applied Mircobiology, W.J. Whitfield et al., vol. 17, No. 1, Jan., 1969, pp. 164–168.

"Pass" Sampler Surface Control, PBI International, No. 93.

Primary Examiner—David A. Reifsnyder
Attorney, Agent, or Firm—Robert L. Shaver; Frank J. Dykas

[57] ABSTRACT

A microbial sampling, filtration, and recovery device which utilizes a wash solution on meat carcasses and a vacuum source to vacuum the wash solution and suspended microbes into a collection device. The collection device includes pre-filters for removing debris, and a microbial filter. The filter is small enough to filter out bacteria, and since this size of filter seriously reduces air flow, an alternate route for air is provided through a hydrophobic filter. Bacteria captured on the filter is back-flushed into a collection vessel where it is concentrated in a subsequent centrifuge step. The concentrated microbial sample is available for use in rapid detection methods.

8 Claims, 5 Drawing Sheets

MICROBIAL SAMPLER AND CONCENTRATOR

This invention was made with government support under a NIH grant, awarded by the National Institute of Health. The government has certain rights in the invention.

BACKGROUND OF THE INVENTION

1. Technical Field

This application relates generally to microbial sampling and filtering devices, and more specifically to suction devices for sampling, filtering, recovering and/or concentrating microbial populations.

2. Background

Outbreaks of human enteric diseases caused by food borne *E. coli* 0157/H7, Salmonella spp., *Campylobacter jejumi/coli* and *Listeria monocytogenes* caused an estimated 5,000,000 illnesses and 3,700 deaths in the U.S. in 1993. Costs due to medical and production losses are estimated between $4.7 and $7.5 billion for the same period. Foods are routinely tested for microbial contamination during the process of preparing a food for consumption by consumers. With meats, a main problem is contamination with *E. coli* bacteria. *E. coli* bacteria are a type of bacteria which is generally present in the digestive tract and fecal material of animals.

Meat processors are under increasing requirements to ensure that their meat processing systems produce meat which is free of *E. coli* or other bacteria pathogenic contamination. One program which has been recently introduced is called "Hazards Analysis and Critical Control Point", or HACCP. This program is based on analyzing a system to determine at what critical points increased control would result in a marked improvement of quality or reduction of contamination of the food product. Under this program, food processors are required to analyze their systems and determine at which critical control points increased testing should be utilized. Once these critical control points are identified, increased testing at these critical points should result in better control of the food process, and more assurance of safety of the final food product.

Under the HACCP Program, the USDA will require over 9,000 meat and poultry establishments to conduct more bacterial lab tests than are presently performed. It is also a major goal of microbial lab test protocols on meat and poultry samples to report at least preliminary test results within a few hours of sampling animal carcasses. This ideal goal would likely save millions of dollars annually for the industry, since recalls and holding times of suspect products would be reduced.

In the processing of beef and other meat products, some of the earliest steps are to hang the beef by its hind legs, skin the beef, remove the entrails from the beef, and split the beef in half down the center line. It has been determined that these steps are critical control points and are steps during which there is a heightened possibility of contamination. Since *E. coli* bacteria exists in the intestinal tract and feces of beef and other animals, the process of skinning the carcass around the anus, and removing the entrails by a worker using a knife, presents a high possibility of the knife becoming contaminated with *E. coli* bacteria. If a knife thus contaminated is laid down on a surface, other equipment which comes in contact with the same surface can be cross-contaminated. For this reason it is critical to be able to sample the beef carcass after the entrails have been removed and after the skin has been removed, to check for the presence of *E. coli* bacteria. It is also critical to be able to test other surfaces and equipment, such as the surfaces of knives, table tops or meat grinders to check for the presence of *E. coli* bacteria.

A variety of non-destructive bacterial sample collection devices are commercially available for sampling large animal carcasses. These include direct agar contact, adhesive contact tape, rinsing, scraping and vacuuming. Vacuuming or aspiration procedures have not been successfully applied to meat animal carcasses. A bacterial, or dust particle vacuuming method, has been used on clean room surfaces. This design would not have application on animal carcasses. The PASS carcass sampler utilizes a sterile spray applied to the carcass surface, followed by collection of the residual liquid by aspiration or pressure. This device is manufactured by pbi of Italy. This sampling device has not been widely accepted in the United States.

The most practical of the current methods for sampling bacteria on larger animal carcasses involve the use of swabs or sponges, with and without templates, which blot, wipe or soak up surface moisture and accompanying microbes from the selected surfaces. These methods can collect a single bacterial colony forming a unit (cfu), if adsorbed during sampling. The principle behind this technique is that for every individual bacterium which was originally on the sterile sponge or cotton swab, each of those individual bacterium will be transferred to the broth and later to the agar in the petri dish. Over a period of about 18 hours at the proper temperature and atmospheric conditions (*E. coli* are normally aerobic bacteria), each of the individual bacterium (cfu) will have grown by cell division into a colony of bacteria, with each colony on an agar plate being visible to the naked eye. Since these bacteria typically double their population in approximately 20 to 30 minutes under ideal conditions, after 18 hours in nutrient broth or on agar plates, sufficient divisions of the original bacteria will have occurred so that the increased numbers of bacteria may be more readily detected.

This sponge method assumes a consistent increased affinity of the collection device surface over that of the sampled surface during collection. Since bacteria affinity and attachment to carcass surfaces are influenced by surface pH, carcass temperature, texture, hydrophobicity, ionic strength, and surface moisture, actual percentages of total microbes collected may be less than representative.

Many of the bacteria which were on the meat could be trapped within folds of the carcass surface or within rough areas, fat cells or connective tissue and simply not be wiped off onto the sponge. Of those bacteria that do get wiped onto the sponge, many of them may stick to the sponge and not be transferred to the broth solution or the petri dishes during a quick rinse or transfer attempts. The incubation time of 18 hours means that if a beef carcass were severely contaminated, it would have moved along the process for 18 hours and may have cross contaminated other beef carcasses or other cutting utensils or handling machinery.

A further limitation to this method is that moisture saturated sponges may spread pathogens from one location to another during sampling of more than one location on a carcass. Reversing sides of the sponge and sampling the three recommended sites on beef and swine carcasses from least to most likely contaminated, offers a good approach to circumventing this problem. But, if used incorrectly, or in cases of abnormal carcass bacterial distribution, it may contribute to further spreading of pathogens.

Current sampling methods result in routine lab specimens which require several hours of enrichment growth before analysis for bacteria identification. Following enrichment procedures, standard or rapid bacterial detection methods may be used. In an attempt to conduct faster analysis during current collection methods and rapid bacteria detection kits, carcass collection sponges may be rinsed or soaked for short time periods in buffered solutions. Results of these procedures are questionable because bacterial numbers are normally low. False negative lab results are more potentially dangerous to consumers than false positives. Therefore, rapid detection methods are not routinely acceptable with current collection techniques without enrichment steps.

Filtration and centrifugation of dilute liquid samples or broth suspected of containing microbes are commonly used in laboratories to separate debris, and to capture and concentrate bacteria for subsequent identification or other testing. Whole bird rinse solutions could be concentrated with these methods, but large fluid volumes from these animal carcasses are cumbersome for routine lab analysis, especially when a large number of samples are involved.

In recent years there have been great improvements in the detection methods for bacteria. For instance, rapid detection systems for *E. coli* 0157/H7 and Salmonella are currently available that require only a few hours to complete. Current rapid detection methods do not require culturing, but allow a sample to be analyzed in a period of several hours. The shortcoming with these rapid detection methods is that a fairly concentrated sample is required. Most of these methods are not directly applicable to bird or sponge rinse solution currently used because of the low number of pathogens normally collected from carcasses, plus the dilution effect of the rinses. Time and labor-consuming procedures for enrichment and bacterial concentration are required before using the rapid Elisa, PCR or similar identification tests. Improved rapid sampling and processing methods are needed to efficiently utilize these new bacteria identification techniques. Current non-destructive bacterial sampling methods for large animal carcasses have several drawbacks which may be magnified under mandates and ramifications of the HACCP programs. These methods:

A. allow sampling of a limited carcass area only;
B. result in bacterial solutions too dilute for same day analysis;
C. require extended lab enrichment time;
D. require high labor and time expenditure.

Regardless of the lab procedure, improved bacterial sampling methods, especially for large animal carcasses which cannot utilize whole body rinse techniques, are needed which can facilitate larger surface area sampling without undue increases in labor and material. In addition, new sampling methods would allow the meat and poultry establishments to routinely benefit from the use of recently developed rapid detection methods for *E. coli* 0157/H7 and other human pathogens.

Accordingly, what is needed is a sampling method and device by which more bacteria are removed from the surface which is sampled. It is a further object that once removed from the surface, more of the collected bacteria which are sampled pass through the sampling system and end up being counted, i.e., improved bacterial recovery. To promote improved recovery, bacteria should be readily collectable from the sampling process and equipment.

It is a further object of this invention to provide a method and apparatus by which bacteria on such surfaces can be detected in a shortened time period.

It is a further object of this invention to provide a sampling method by which large volumes of dilute rinse and bacteria suspensions could provide concentrated bacterial populations, and in a shortened period of time over existing sampling methods and equipment.

Additional objects, advantages and novel features of the invention will be set forth in part in the description as follows, and in part will become apparent to those skilled in the art upon examination of the following, or may be learned by practice of the invention. The objects and advantages of the invention may be realized and attained by means of the instrumentalities and combinations particularly pointed out in the appended claims.

DISCLOSURE OF INVENTION

These and other objects are accomplished by a microbial sampler for sampling a surface. The microbial sampler includes a surface attachment for suctioning microbes from the surface using an aqueous wash solution in which the microbes are suspended. It also includes a filter device for capturing microbes and separating the microbes from the aqueous wash solution in which they are suspended. It also includes a way of recovering and concentrating the microbes from the filter device.

The microbial sampler can use as a filter device a filter which is designed to capture microbes of a selected size. For instance, a filter for capturing bacteria would be of a different pore size than a filter designed for collecting yeast or parasite samples. The problem with filters with pores small enough to filter bacteria is that they don't allow a sufficient flow of air to pass through to provide sufficient suction on the sampled surface. To solve this air flow problem, the filter device is designed to include a hydrophobic filter which allows the passage of air, but which does not allow the passage (under normal conditions of use) of the aqueous wash solution in which the microbes are suspended. The filter device can include a pre-filter which is designed to capture contaminants of a selected size. For instance, when sampling microbes from the surface of an animal carcass, cells of fat, blood cells, hair, connective tissue and pieces of skin may be drawn into the sampling device. The pre-filter would reduce these tissues, cells and cell parts in the final sample.

The microbial sampler described above utilizes a means of recovering and concentrating the microbial sample. This means includes a rinse solution which is back flushed through the filter on which the microbes are collected, dislodging the microbes from the filter, and transporting them in a suspended state with the rinse solution. The rinse solution with the suspended microbes passes into a collection receptacle for collecting and for further concentration of the microbes. Typically, the collection receptacle is centrifuged for further concentration of the microbes. When concentrated into a pellet, the microbes would be available for detection and quantification by a variety of analytical means.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawing and description are to be regarded as illustrative in nature, and not as restrictive.

BEST MODE FOR CARRYING OUT INVENTION

Figure 1:
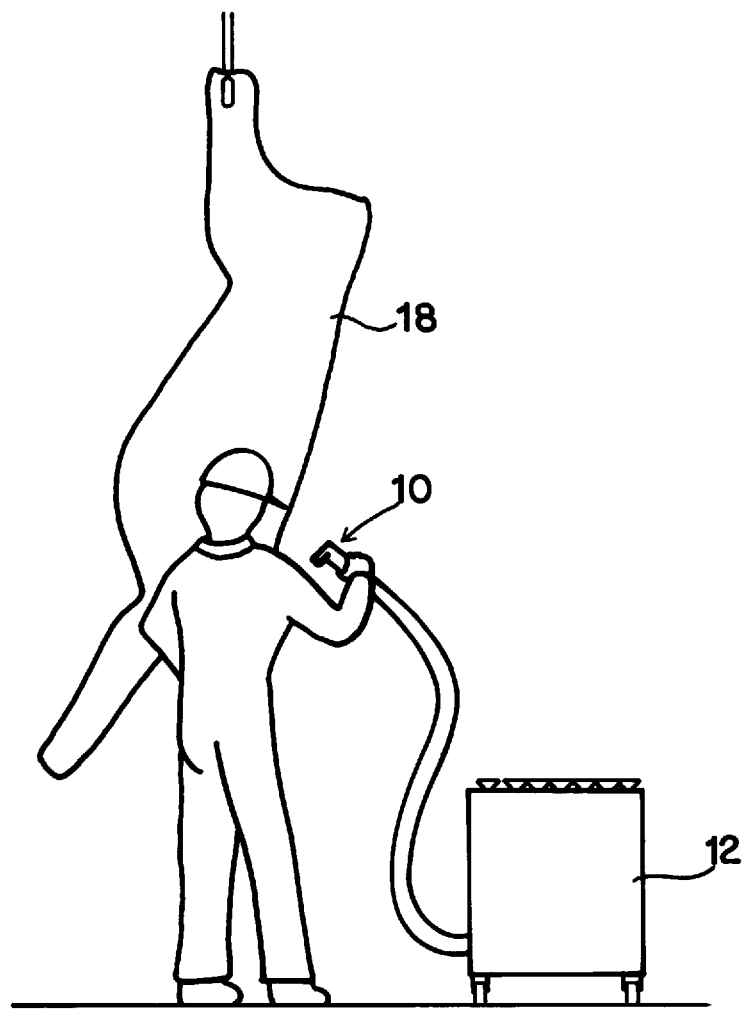
FIG. 1 is a side view showing the microbial sampler in use on a side of beef.

Referring to FIGS. 1 through 7, the invention is shown to advantage. The microbial sampler is generally referred to as 10, and comprises a surface nozzle 16 (shown in FIGS. 1, 2 and 3), a pre-filter chamber 20, a filter chamber 22, pre-filters 26 and 24, filter 42 (shown in FIG. 3). The microbial recovery and concentration process of the device is shown in FIGS. 4 through 7 and includes the filter chamber 22, the wash chamber 60, and the recovery chamber 62, with a conical concentration tip 68.

Figure 2:
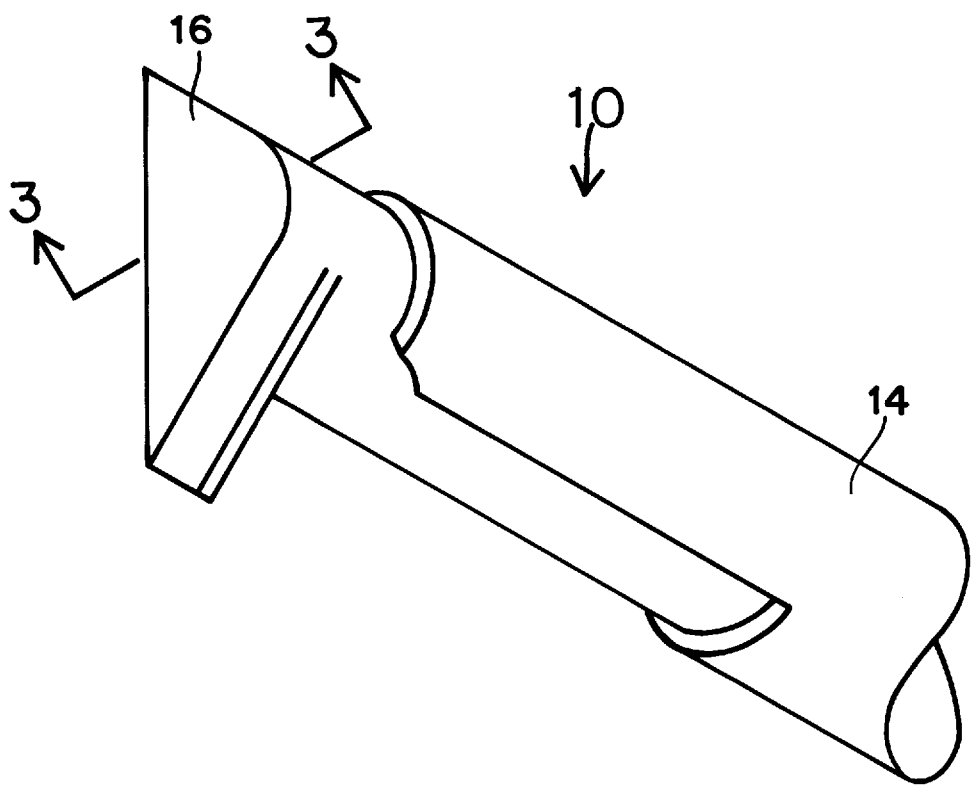
FIG. 2 is a representational view of the microbial sampler in the holder.
Figure 3:
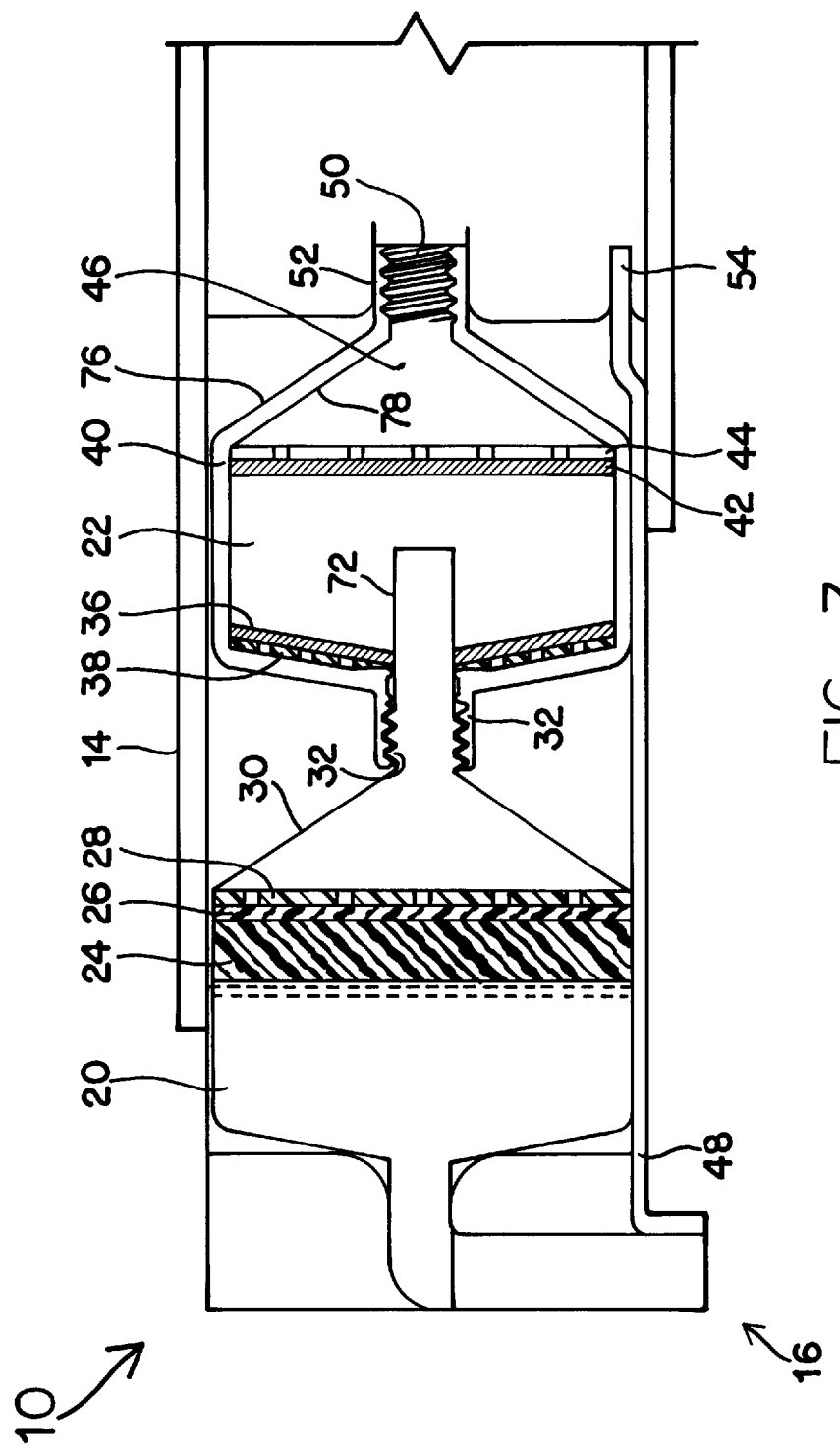
FIG. 3 is a side cross-sectional view of the microbial sampler.

The surface nozzle 16 is shown in FIGS. 1, 2 and 3. The purpose of the surface nozzle is to use air flow created by vacuum to draw air across the surface being sampled. The preferred embodiment at this time is a simple, funnel-shaped nozzle 16 shown in FIG. 2. Another preferred embodiment includes a wash tube 48 which directs a wash solution at the surface being sampled, as shown in FIG. 3. The wash solution is lifted by air flow with the bacteria which it suspends and is drawn into pre-filter chamber 20. Surface nozzle 16, as well as pre-filter chamber 20, filter chamber 22, wash chamber 60 and recovery chamber 62 are preferably made of polyethylene or polypropylene, but a number of materials can be utilized and the material used is not critical.

The microbial sampler is cylindrical in shape and is approximately 1½ to 2 inches wide by 8 to 10 inches tall. The pre-filter chamber is circular in cross-section when seen from above, and is generally cylindrical. At its bottom end is found a sample funnel 30, shown in FIG. 3. Funnel neck 72 extends beyond funnel 30 and past the pre-filter chamber threads 32. Inside the pre-filter chamber 20 is located a pre-screen 24, a pre-filter 26, and a pre-filter support 28. The pre-screen 24, the pre-filter 26 and pre-filter support 28 are circular when seen from the top and completely block the pre-filter chamber, thus forcing any fluid which is drawn through the pre-filter chamber 20 by vacuum, to pass through each of these three elements. The pre-screen 24 is a fairly course material, such as woven cotton or other fabric. The purpose of the pre-screen 24 is to block the passage of fairly large contaminants, such as fat particles, hair, connective tissue or other contaminants. The pre-filter 26 has pores of approximately 1.5 microns, which are sufficiently small to stop contaminants such as red blood cells, (3 to 10 microns in size) or other cells, such as individual fat cells or pieces of cellular material. However, pre-filter 26 allows particles smaller than 1.5 micron to pass through. *E. coli* bacteria are 0.45 to 0.7 microns in diameter, and thus pass readily through pre-filter 26. A pre-filter with a pore size of 1.5 micron is sufficiently large to allow a sufficient flow of air to pass through the pre-filter. Pre-filter support 28 also has pores, and they are much larger than those of either the pre-screen or the pre-filter. The pre-filter support 28 merely provides a physical structure against which the pre-filter 26 and the pre-screen 24 can be supported. The pre-filter chamber 20 constitutes segment 2 of the microbial sampler.

Segment 3 of the microbial sampler includes the filter chamber 22 and its components. Filter chamber 22 is circular in cross-section when seen from above, and is generally cylindrical in shape. The walls of filter chamber 22 taper into a filtrate funnel 46 at its lower end. The filtrate funnel 46 ends in a connection 50 and threads 52. Above the filtrate funnel 46 is located a filter support 44 and a filter 42. Filter 42 will typically be a nitro hydrophilic cellulose filter with pore sizes of approximately 0.45 microns. This pore size is designed to catch *E. coli* bacteria on its surface. Filters made from other materials and with other pore sizes could be utilized to capture microbes of different sizes or surface characteristics. Opposite filter 42 is a hydrophobic filter 36 and a hydrophobic filter support 38. Hydrophobic filter 36 will typically be made of a Teflon® based or similar material and have pores of approximately 1.5 micron. These pores allow air to pass through, but the position of the filter and the hydrophobic characteristic of the filter material prevent the wash solution or the suspended microbes from passing through the hydrophobic filter. In communication with the filter chamber 22 through the hydrophobic filter 36, is an air chamber 40.

The filter 42 will typically have pores which are too small to pass sufficient air to maintain the proper air flow at the surface nozzle 16. To provide this air flow, air chamber 40 is provided which draws air from the filter chamber 22 through the hydrophobic filter 36 and through the air chamber 40 towards the vacuum source 12 shown in FIG. 1. The wash solution in which the microbes are suspended is drawn through filter 42, and is repelled from hydrophobic filter 36. In the preferred embodiment of the invention, air chamber 40 is formed between outer wall 76 and inner wall 78 of the filter chamber 22, shown in FIG. 3.

Figure 4:
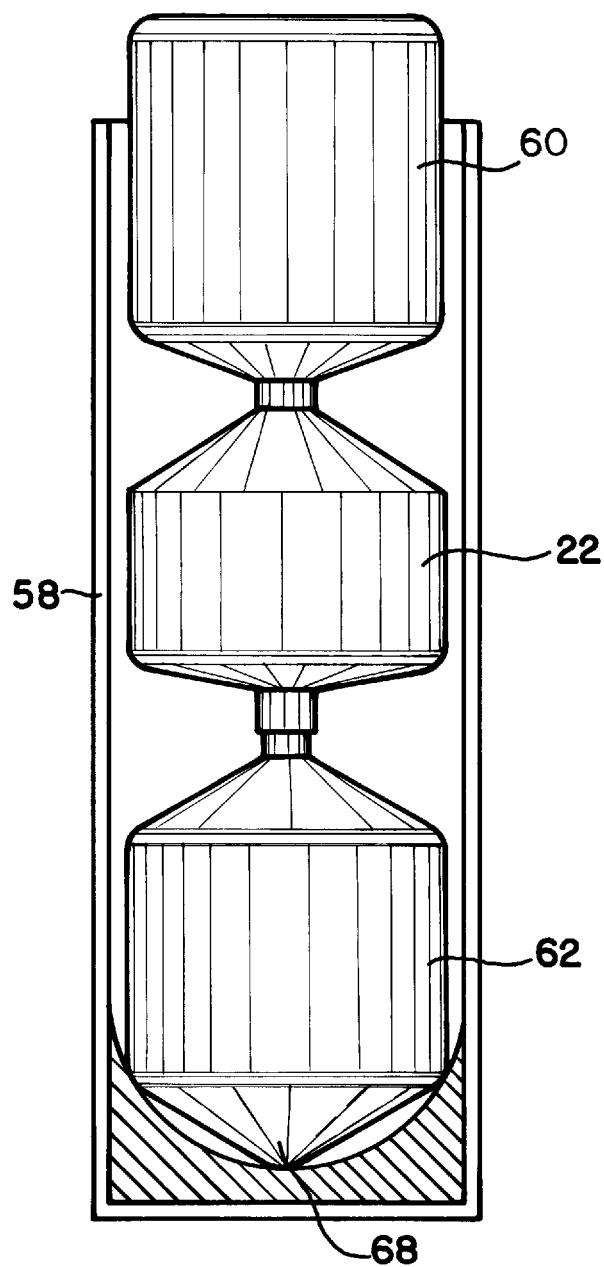
FIG. 4 is a side view of the microbial sampler in a centrifuge tube.
Figure 5:
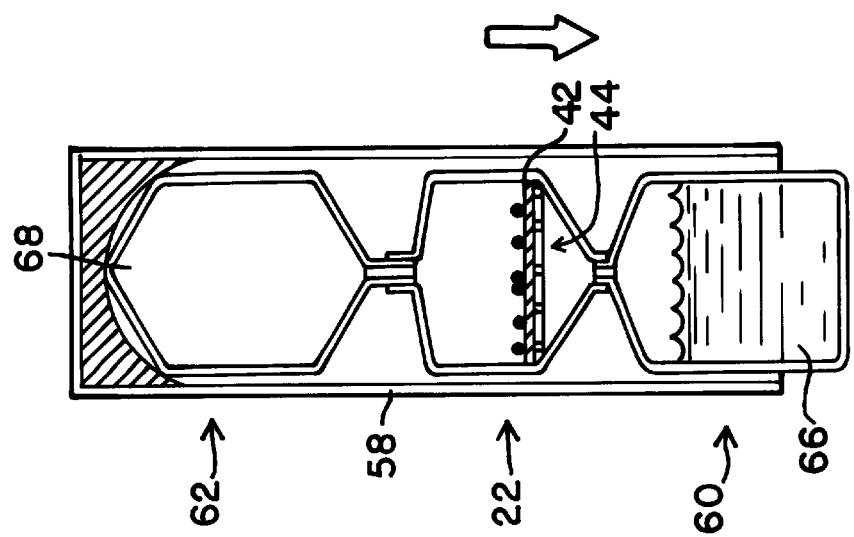
FIG. 5 is a cross-sectional view of a microbial sampler and a centrifuge tube before centrifugation.

The microbial sampler also includes a rinse chamber 60, as seen in FIGS. 4–7, which attaches to the filter chamber 22. Rinse chamber 60 is a generally cylindrical structure with threads 52 on one end. It contains rinse solution 66 as shown in FIG. 5. Rinse chamber 60 is preferably made of polyethylene or polypropylene plastic, but a number of other materials would also be suitable.

The microbial sampler also includes a recovery chamber 62, as shown in FIG. 4. Recovery chamber 62 is a generally cylindrical container with threads 32 at one end and a conical concentration tip 68 at the other end. It screws into filter chamber threads 32 and is empty when first attached.

In operation, the microbial sampling unit 10 is used as follows. A microbial sampling unit comprised of a pre-filter chamber, a filter chamber, and a surface nozzle, is assembled. Normally these three units would be pre-assembled and ready to be used in sterile packaging at the point of sampling, such as on a meat processor's shop floor from a sample cart. A vacuum source 12 would be attached to the connection 50 of the filter chamber 22. Wash solution (not shown) would be applied to the surface to be sampled either by the use of a hand-held wash bottle, or through wash tube 48 which could be built into the microbial sampling unit and sprayed on to the surface to be tested from an orifice near the surface nozzle 16. The vacuum source 12 would evacuate the interior of filter chamber 22, and primarily through air chamber 40 would draw air through the funnel neck from the pre-filter chamber 20 and from the pre-filter chamber 20 through the pre-screen 24 and the pre-filter 26. Through this route of air evacuation, the air would be evacuated from surface nozzle 16. This would cause an air flow over the surface being sampled which would draw the wash solution (not shown) with its suspended microbes 64 into the surface nozzle 16. The wash solution (not shown) and suspended microbes would then travel with the flow of air created by the vacuum source 12 through the pre-screen 24 and the pre-filter 26. Any particles of large cellular material such as pieces of fat, fat cells, red blood cells, connective tissue, hair, broken pieces of red blood cells or other debris would be stopped by either the pre-screen 24 or the pre-filter 26. The wash solution (not shown) with the suspended microbes 64 would pass through the pre-screen 24 and the pre-filter 26, be drawn with the air through the sample funnel 30, and the funnel neck 72 from the pre-filter chamber 20 and into the filter chamber 22. At that point the wash solution (not shown) would be drawn through the filter 42 and the microbes 64 would be deposited on the surface of the filter 42. Air from the filter chamber 22 would be drawn through the hydrophobic filter 36, into the air chamber 40, and out the connection 50 to the vacuum source 12. Any wash solution with suspended bacteria which came into contact with hydrophobic filter would be repelled by the material of the filter and run down the side of filter chamber 22, rather than being drawn through the pores of the hydrophobic filter 36.

After the area to be sampled had been thus contacted with wash solution (not shown) and had that solution drawn away by a flow of air created by a vacuum 12, the sampling part of the operation would be complete.

Figure 7:
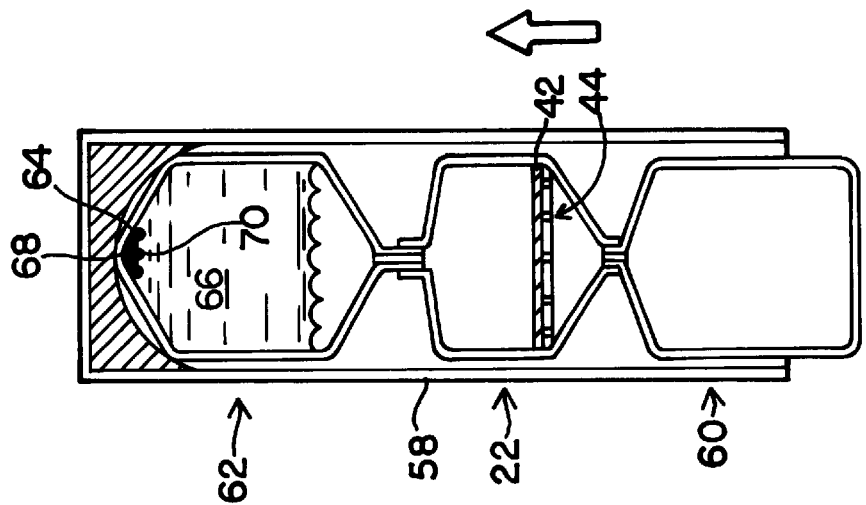
FIG. 7 is a cross-sectional view of a microbial sampler and a centrifuge tube after centrifugation.
Figure 6:
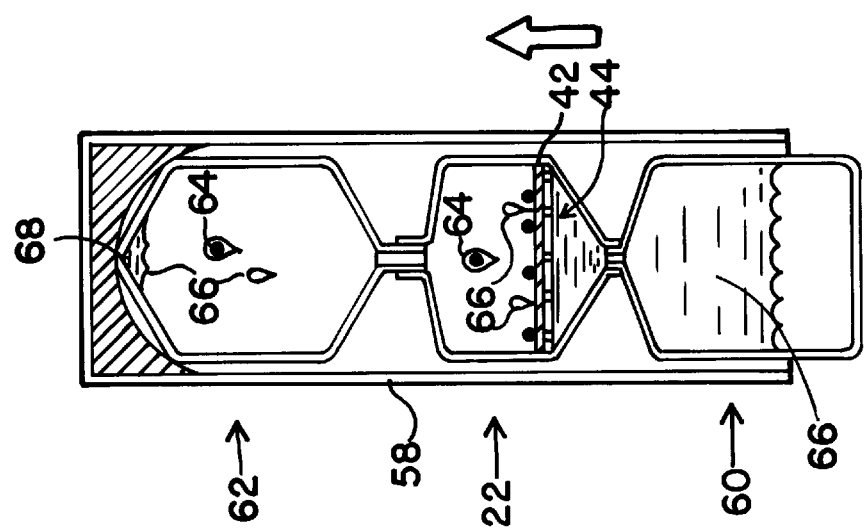
FIG. 6 is a cross-sectional view of a microbial sampler and a centrifuge tube during centrifugation.

The next step of the operation then, which is the microbial recovery and concentration step, would begin as shown in FIGS. 4–7. The recovery and concentration step would begin by removing filter chamber 22 from pre-filter chamber 20 and disconnecting filter chamber 22 at 50 from the vacuum source 12. At this point, some sort of threaded or snap closure would be used to seal the orifices at either end of the filter chamber 22. Alternatively, rinse chamber 60 and recovery chamber 62 could be attached to filter chamber 22 at that time. Rinse chamber 60 or recovery chamber 62 might also be attached to filter chamber 22 when filter chamber 22 had been transported to a laboratory for detection and/or quantification of the microbes. The steps of the microbial recovery and concentration are shown in FIGS. 5 through 7. In FIG. 5, the filter chamber 22 is shown connected to the rinse chamber 60 and the recovery chamber 62. These three chambers joined together are shown inside centrifuge tube 58. The large arrow to the right of FIG. 5 indicates the force of gravity which is on these three chambers. This force of gravity results in rinse solution 66 remaining in rinse chamber 60. The arrow next to FIG. 6 indicates the pull induced by centrifugal force which causes rinse solution 66 to begin leaving rinse chamber 60 and to flow into filter chamber 22, and through filter support 44 and filter 42. As rinse solution 66 flows through filter 42, microbes 64 are dislodged and suspended in the rinse solution 66. Rinse solution 66 with suspended microbes 64 passes from filter chamber 22 into the recovery chamber 62. As shown in FIG. 7, the centrifugal force from the centrifuge forces microbes 64 into the conical concentration tip 68 of the recovery chamber 62. As centrifugation is continued, most of rinse solution 66 is deposited in recovery chamber 62. Simultaneously, air from recovery chamber 62 passes through hydrophobic filter 36, through air chamber 40, and replaces the wash solution 66 volume in rinse chamber 60. A small quantity of rinse solution 66 is absorbed by and remains in filter 42. After a period of time, centrifugation may be halted, and microbes 64 will remain in a pellet 70 located in the conical concentration tip of the recovery chamber 62.

Once the bacteria or other microbes are formed into a pellet 70, they can be recovered and analyzed by rapid detection analytical methods such as Enzyme Linked, Immunosorbent Assay (ELISA), polymerase chain reaction (PCR), Radioimmunoassay (RIA), immunofluorescence, or other rapid detection methods. These methods are rapid detection methods which can give detection and/or quantification results much more quickly than methods involving bacterial growth in growth media. However, these methods require a fairly concentrated sample.

The microbial sampler thus obtains a more representative sample from the surface to be sampled by the use of air and rinse solution movement generated by a vacuum source. Bacteria or other microbes are deposited on a filter surface in a unit which is designed to lend itself to further concentration of the microbes and rapid analysis by rapid detection methods.

While there is shown and described the present preferred embodiment of the invention, it is to be distinctly understood that this invention is not limited thereto but may be variously embodied to practice within the scope of the following claims.

I claim:

1. A microbial sampler for sampling a surface, comprising:
    a surface attachment for suctioning microbes from said surface using an aqueous wash solution in which said microbes are suspended;
    a filter means for capturing microbes and separating said microbes from said aqueous wash solution;
    an air chamber which allows passage of air, but not wash solution around said filter means; and
    a means for recovering and concentrating said microbes from said filter means.

2. The microbial sampler for sampling a surface of claim 1 in which said filter means comprises a filter designed to capture microbes of a selected size.

3. The microbial sampler for sampling a surface of claim 2 in which said filter means further comprises a pre-filter designed to capture contaminants of a selected size.

4. A microbial sampler for sampling a surface, comprising:
    a surface attachment for suctioning microbes from said surface using an aqueous wash solution in which said microbes are suspended;
    a filter means for capturing microbes and separating said microbes from said aqueous wash solution, comprising a filter designed to capture microbes of a selected size;
    a hydrophobic filter which allows the passage of air but does not allow the passage of said aqueous wash solution with suspended microbes; and
    a means for recovering and concentrating said microbes from said filter means.

5. The microbial sampler for sampling a surface of claim 4 in which said means of recovery and concentrating comprises:
    a rinse solution for back flushing said filter and dislodging and suspending said microbes from said filter; and
    a collection receptacle for recovering said rinse solution and suspended microbes and for concentrating said microbes.

6. The microbial sampler for sampling a surface of claim 5 in which said collection receptacle is centrifugible for concentration of said microbes.

7. A microbial sampler for sampling a surface comprising:

a surface attachment for suctioning microbes from said surface using an aqueous wash solution in which said microbes are suspended;

a filter means comprising a filter designed to capture microbes of a selected size, for capturing microbes and separating said microbes from said aqueous wash solution, further comprising a hydrophobic filter which allows the passage of air but does not allow the passage of said aqueous wash solution with suspended microbes, and still further comprising a pre-filter designed to capture contaminants of a selected size; and a means for recovering and concentrating said microbes from said filter means, comprising;

a rinse solution for back flushing said filter and dislodging and suspending said microbes from said filter; and a collection receptacle for recovering said rinse solution and suspended microbes and for concentrating said microbes.

8. The microbial sampler for sampling a surface of claim 7 in which said collection receptacle is centrifugible for concentration of said microbes.

* * * * *